United States Patent [19]

Imamura et al.

[11] 3,991,114

[45] Nov. 9, 1976

[54] PROCESS FOR AMINATING BIS(2-CHLORO-1-NITROSOCYCLOHEXANE)

[75] Inventors: Shinzo Imamura; Ichiro Kawamoto, both of Nagoya; Koji Natsume, Toyoake; Shinnosuke Sakai, Nagoya, all of Japan

[73] Assignee: Toray Industries, Inc., Tokyo, Japan

[22] Filed: Sept. 19, 1975

[21] Appl. No.: 615,079

[30] Foreign Application Priority Data

Sept. 20, 1974 Japan.............................. 49-107621

[52] U.S. Cl............................................ 260/566 A
[51] Int. Cl.$^2$...................................... C07C 131/00
[58] Field of Search........................ 260/566 A, 647

[56] References Cited
UNITED STATES PATENTS 2,485,180  10/1949  Allison................................ 260/647

Primary Examiner—Gerald A. Schwartz
Attorney, Agent, or Firm—Haseltine, Lake & Waters

[57] ABSTRACT

There is provided an improvement in the process for the amination of bis(2-chloro-1-nitrosocyclohexane) wherein bis(2-chloro-1-nitrosocyclohexane) prepared by reacting cyclohexene with nitrosyl chloride in the presence of liquid sulfur dioxide is treated with ammonia. Sulfur dioxide contained in the nitrosation reaction mixture in the form of a slurry or solution containing bis(2-chloro-1-nitrosocyclohexane) is evaporated in the presence of an inert organic solvent, incorporated into the reaction mixture, and is substantially removed from the reaction mixture. Thereafter, the slurry or solution of bis(2-chloro-1-nitrosocyclohexane) in the inert organic solvent thus prepared is treated with ammonia.

7 Claims, No Drawings

PROCESS FOR AMINATING BIS(2-CHLORO-1-NITROSOCYCLOHEXANE)

This invention relates to a process for connecting, in the production of α-aminocyclohexanone oxime from cyclohexene, the step of reacting cyclohexene with nitrosyl chloride into bis (2-chloro-1-nitrosocyclohexane) and the step of aminating the bis(2-chloro-1-nitrosocyclohexane) into α-aminocyclohexanone oxime. More particularly, it relates to a process wherein a reaction mixture, which is prepared by the step of reacting cyclohexene with nitrosyl chloride in the presence of liquid sulfur dioxide and which contains a considerable amount of bis(2-chloro-1-nitrosocyclohexane) and a minor amount of side-reaction products, is maintained in the presence of an organic solvent inert to the reaction mixture under conditions such that sulfur dioxide is evaporated whereby the sulfur dioxide is removed from the reaction mixture, and then, the slurry or solution of bis(2-chloro-1-nitrosocyclohexane) in the inert organic solvent thus prepared, is treated with ammonia.

α-Aminocyclohexanone oxime (III) may be prepared by the steps of reacting cyclohexene (I) with nitrosyl chloride in the presence of liquid sulfur dioxide and then, aminating the bis(2-chloro-1-nitrosocyclohexane) (II) so prepared. In general, α-aminocyclohexanone oxime is converted into α-amino-ε-caprolactam (IV) by the Beckmann rearrangement, and α-amino-ε-caprolactam is converted by chemical or biochemical hydrolysis into lysine (V) which is one of the essential amino acids. The course of these steps is expressed as follows.

duces the yield of α-aminocyclohexanone oxime to a great extent.

Bis(2-chloro-1-nitrosocyclohexane) is liable to decompose due to heat and the air, although it is a solid insoluble or slightly soluble in most organic solvents at an ambient temperature. Therefore, this compound is preferably handled at the lowest possible temperature and in the form of a solution or slurry, and should not be subjected to isolation operations such as filtration, crystallization and drying which are popularly employed for the isolation of solids. Further, bis(2-chloro-1-nitrosocyclohexane) is partially dissociated into its monomer, i.e. 2-chloro-1-nitrosocyclohexane, as follows.

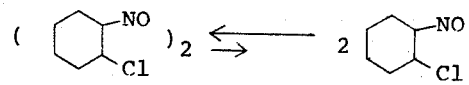

This monomer is very unstable and liable to decompose when subjected to the isolation operations set forth above.

It is a main object of the present invention to provide a process for preparing α-aminocyclohexanone oxime from cyclohexene with an improved yield. That is, sulfur dioxide present in the nitrosation reaction mixture is substantially removed therefrom and thereafter, the nitrosation product is supplied to the succeeding amination step without isolation of bis(2-chloro-1-nitrosocyclohexane), and therefore, α-aminocyclohexanone oxime can be produced with an improved yield.

In accordance with the present invention, there is provided an improvement in the process for the amination of bis(2-chloro-1-nitrosocyclohexane) wherein bis(2-chloro-1-nitrosocyclohexane) prepared by react-

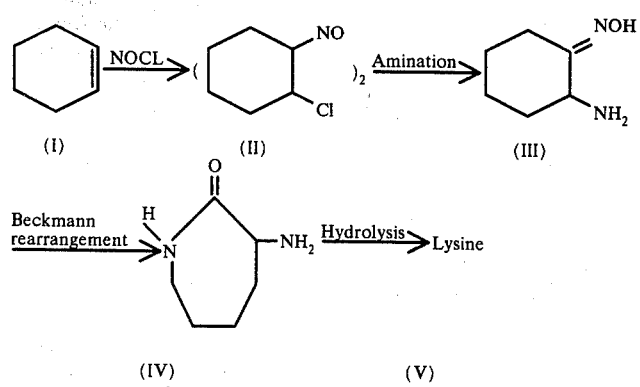

Of these steps, the step of preparing bis(2-chloro-1-nitrosocyclohexane) and the step of aminating this compound are carried out in acidic and basic atmospheres, respectively. Therefore, one of the keys for advantageously producing lysine is how to connect the two steps mentioned above.

It is already known, as proposed in U.S. Pat. No. 2,485,180, that the nitrosation of cyclohexene by nitrosyl chloride is carried out in a liquid sulfur dioxide medium. This procedure is advantageous in that bis(2-chloro-1-nitrosocyclohexane) is produced with a yield higher than those obtained by other known procedures. However, sulfur dioxide is not convenient to handle because it possesses a low boiling point, i.e. −10° C, and toxicity, and acts corrosively in the presence of water. Further, when sulfur dioxide is present in any appreciable amount in the reaction mixture to be treated in the amination step, the sulfur dioxide reing cyclohexane with nitrosyl chloride in the presence of liquid sulfur dioxide is treated with ammonia, said improvement comprising
evaporating sulfur dioxide to substantially remove it from the reaction mixture in the form of a slurry or solution containing bis(2-chloro-1-nitrosocyclohexane) in the presence of an organic solvent, incorporated into said reaction mixture, which solvent in inert to said reaction mixture, and then, treating with ammonia the slurry or solution of bis(2-chloro-1-nitrosocyclohexane) in the organic solvent, thus prepared.

The reaction mixture containing bis(2-chloro-1-nitrosocyclohexane) is prepared by the reaction of cyclohexene with nitrosyl chloride in the presence of liquid sulfur dioxide. The procedures by which the above reaction mixture is prepared is not especially critical, so known procedures, for example, as disclosed in U.S. Pat. No. 2,485,180, may be employed. In general, such as reaction mixture contains, besides bis(2-chloro-1-nitrosocyclohexane), 1 to 20 g of sulfur dioxide, 0 to 1 g of cyclohexene, 0 to 1.5 g of an organic solvent, 0.05 to 0.1 g of 2-chloro-1-nitrosocyclohexane and 0.01 to 0.1 g of side-reaction products, all per g of bis(2-chloro-1-nitrosocyclohexane).

The reaction mixture containing bis(2-chloro-1-nitrosocyclohexane) and sulfur dioxide is fed, together with an organic solvent inert to the reaction mixture, to an evaporater where the sulfur dioxide is evaporated to be substantially removed from the reaction mixture. The procedure whereby the sulfur dioxide is evaporated in the evaporator is not critical, so various procedures may be employed. For example, in one procedure, the reaction mixture having an inert organic solvent previously incorporated therein, is fed to an evaporator. In another procedure, only the reaction mixture is fed to the feed inlet of an evaporator and an inert organic solvent is incorporated into the reaction mixture at a midway point in the path of the flow of the reaction mixture in the evaporator. That is, the organic solvent is added to the reaction mixture after a part of the sulfur dioxide is removed from the reaction mixture. In still another procedure, employing two or more evaporators connected in series, the reaction mixture is fed to the first evaporator and the organic solvent is fed to the second or third evaporator. In any case, an inert organic solvent should be combined with the reaction mixture so that the reaction mixture maintains sufficient fluidity over the entire path in the evaporator.

The evaporation of sulfur dioxide is carried out under an atmospheric or reduced pressure, depending upon the amount of sulfur dioxide to be evaporated, the boiling point of an inert organic solvent and the temperature at which sulfur dioxide is evaporated. The mixture of an inert organic solvent and the reaction mixture is preferably maintained at a temperature not exceeding 50° C in the evaporator, so as to avoid the decomposition of the nitrosation product.

In order to minimize the amount of an inert organic solvent used, it is preferable to equip the evaporator with a rectification column or partial condenser thereby making a substantial amount of the inert organic solvent evaporated accompanying the sulfur dioxide flow back to the reaction mixture. The sulfur dioxide taken out of the evaporator still contains a slight amount of the inert organic solvent. The recovered sulfur dioxide may be fed to the step of nitrosation of cyclohexene either after it is separated from the inert organic solvent or as it is in the state of a mixture containing the organic solvent.

The evaporation of sulfur dioxide should preferably be to such an extent that the reaction mixture taken out from the evaporator contains the least amount, usually less than approximately 0.5% by weight, based on the weight of bis(2-chloro-1-nitrosocyclohexane), of sulfur dioxide. If sulfur dioxide is present in an amount exceeding approximately 0.5% by weight in the reaction mixture, the yield of α-aminocyclohexane oxime is reduced. In one preferable embodiment, the reaction mixture taken from the evaporator contains, besides bis(2-chloro-1-nitrosocyclohexane), 0 to 0.005 g of sulfur dioxide, 0 to 1 g of cyclohexene, 1 to 20 g of the inert organic solvent, 0.05 to 0.1 g of 2-chloro-1-nitrosocychlohexane and 0.01 to 0.1 g of side-reaction products all per g of bis(2-chloro-1-nitrosocyclohexane).

The organic solvent to be incorporated into the nitrosation reaction mixture is chosen from those which are inert to said reaction mixture, i.e. bis(2-chloro-1-nitrosocyclohexane) and sulfur dioxide, and ammonia. The organic solvents possessing a boiling point of lower than 120° C at an atmospheric pressure are preferable in view of the recovery effeciency of sulfur dioxide and the easiness of recovering the organic solvent after the amination. Such organic solvents include, for example, hydrocarbons such as benzene, cyclohexane, cyclohexene, toluene, hexane, pentane and heptane; halogenated hydrocarbons such as chloroform, carbon tetrachloride and trichloroethylene; and lower alcohols having 1 to 4 carbon atoms such as methanol, ethanol, propanol and butanol. These organic solvents may be used alone or in combination.

Among the organic solvents listed above, cyclohexene which is a raw material for the preparation of bis(2-chloro-1-nitrosocyclohexane) is preferable. This is because, first cyclohexene has a low melting point, i.e. −80° C and is not frozen when the nitrosation reaction mixture is maintained at a low temperature, and second, it is capable of readily separating from ammonia after the amination and can be readily reused for incorporation into the nitrosation reaction mixture.

The amount of the organic solvent to be incorporated into the nitrosation reaction mixture is preferably within the range of 1 to 20 g per g of bis(2-chloro-1-nitrosocyclohexane). When the amount of the organic solvent is too large, the cost for recovering the solvent increases and the evaporation equipment becomes large. In contrast, when the amount of the organic solvent is too small, the nitrosation reaction mixture becomes difficult to handle in the evaporation equipment and the efficiency of $SO_2$ removal decreases.

The nitrosation reaction mixture, from which sulfur dioxide has been substantially removed, is in the form of a slurry or solution in the organic solvent. This slurry or solution is then subjected to the amination step. The amination of bis(2-chloro-1-nitrosocyclohexane) is preferably carried out by the procedure and under the conditions disclosed in Japanese Patent Publication 10789/1973. That is, it is preferred that the slurry of solution of bis(2-chloro-1-nitrosocyclohexane) in the inert organic solvent is treated with more than 20 moles, per mole of bis(2-chloro-1-nitrosocyclohexane) of ammonia at a temperature of 50° to 90° C and at a high pressure, for a period of 15 minutes to 2 hours.

As seen from the above illustration, undesirable decomposition of bis(2-chloro-1-nitrosocyclohexane) can be avoided or mitigated, and the sulfur dioxide is substantially removed from the nitrosation reaction mixture and is recovered. Thus, the amination product is of high purity and the yield of α-aminocyclohexanone oxime is enhanced. Further, the process of the invention is advantageous from a commercial point of view.

The invention is further disclosed in the following examples, which are illustrative but not limitative thereof. In the examples, % is by weight.

COMPARATIVE EXAMPLE 1

A 300 ml volume flask was charged with 150 ml of liquid sulfur dioxide and 20.54 g (0.25 mol) of cyclohexene. To the flask, while being stirred at a temperature of −30° C, 41.08 g (0.50 mol) of cyclohexene and 32.73 g (0.50 mol) of nitrosyl chloride were continuously added at a constant rate, over a period of 2.5 hours. The stirring was continued at −30° C for an additional 30 minutes.

The reaction mixture so prepared was filtered whereby the crystals formed were separated. The filtrate was evaporated to dryness at a reduced pressure. The crystals and the dried residue were mixed well and then dried at 50° C and at a reduced pressure for 3 hours to obtain 68.65 g of light brown solid. The solid proved, by analysis, to contain 0.82% of sulfur dioxide.

10 g of the above solid was dispersed in 40 g of cyclohexene to obtain a slurry. A 500 ml volume autoclave was charged with the slurry followed by the addition of 172.9 g of liquid ammonia. After the autoclave was sealed, the content was maintained at 70° C for 1 hour. Then, the inner pressure was released to expel the unreacted ammonia and the content was taken out therefrom. The content was evaporated to dryness at a reduced pressure to obtain 11.18 g of a solid product. This product proved, by analysis, to contain 88.72% of α-aminocyclohexanone oxime hydrochloride. The yield of this compound was 82.71% based on the nitrosyl chloride used.

COMPARATIVE EXAMPLE 2

A 300 ml volume flask was charged with 150 ml of liquid sulfur dioxide and 8.22 g (0.10 mol) of cyclohexene. To the flask, while being stirred at a temperature of −30° C, 6.55 g (0.10 mol) of nitrosyl chloride and 8.22 g (0.10 mol) of cyclohexene were continuously added at a constant rate over a period of one hour. The stirring was continued at −30° C for an additional 30 minutes. Then, 60 g of cyclohexene were added to the reaction mixture, and the flask was immersed, while being stirred, in a water bath at 40° C for 1 hour, whereby the sulfur dioxide was evaporated. The gaseous sulfur dioxide was removed through a condenser, but cyclohexene accompanying the gaseous sulfur dioxide was condensed so as to flow back into the reaction mixture. The light yellow reaction mixture so prepared proved by analysis to contain 3.30%, based on the weight of the solid product, of sulfur dioxide.

A 500 ml of volume autoclave was charged with the entire amount of the above reaction mixture and 255.2 g of liquid ammonia. After the autoclave was sealed, the content was maintained at 70° C for 1 hour while being stirred. Then, the inner pressure was released to expel the unreacted ammonia and the content was taken out therefrom. The content was evaporated to dryness at a reduced pressure to obtain 16.84 g of a solid product. This product proved, by analysis, to contain 82.76% of α-aminocyclohexanone hydrochloride. The yield of this compound was 84.65% based on the nitrosyl chloride used.

EXAMPLE 1

Following the procedure set forth in Comparative Example 2, a reaction mixture of cyclohexene and nitrosyl chloride was prepared. Then, 60 g of cyclohexene were added to the reaction mixture, and, while being stirred, maintained at 25° C under a reduced pressure of 40 to 60 mmHg abs. for one hour, whereby the sulfur dioxide was evaporated and removed through a condenser. Cyclohexene accompanying the gaseous sulfur dioxide was condensed in the condenser to flow back into the reaction mixture. The light green reaction mixture so otained proved, by analysis, to contain 0.12%, based on the weight of the solid product, of sulfur dioxide.

The entire amount of the above reaction mixture ws treated with liquid ammonia in a manner similar to that in Comparative Example 2 thereby obtaining 16.72 g of a solid product. This product proved, by analysis, to contain 92.79% of α-aminocyclohexanone oxime hydrochloride. The yield of this compound was 94.24% based on the nitrosyl chloride used.

EXAMPLE 2

Following the procedure set forth in Comparative Example 2, the reaction of cyclohexene and nitrosyl chloride was prepared. Then, 60 g of cyclohexene were added to the reaction mixture, and, while being stirred, the reaction mixture was maintained at 25° C in a water bath for one hour, whereby the sulfur dioxide was evaporated and removed through a condenser. The reaction mixture was further maintained at a reduced pressure of 40 to 60 mmHg abs. for 30 minutes while being stirred, to complete the evaporation of sulfur dioxide. Cyclohexene accompanying the gaseous sulfurous acid was condensed so as to flow back into the reaction mixture. The reaction mixture so obtained proved, by analysis, to contain 0.09%, based on the weight of the solid product, of sulfur dioxide.

The entire amount of the above reaction mixture was treated with liquid ammonia in a manner similar to that in Comparative Example 2, thereby obtaining 16.59 g of a solid product. This product proved, by analysis, to contain 92.97% of α-aminocyclohexanone oxime hydrochloride. The yield of this compound was 93.70% based on the nitrosyl chloride used.

EXAMPLE 3

Following the procedure set forth in Comparative Example 2, a reaction mixture of cyclohexene and nitrosyl chloride was prepared. Then, 60 g methanol were added thereto, and the sulfur dioxide was removed therefrom in a manner similar to that in Example 1. The light yellow reaction mixture so obtained proved, by analysis, to contain 0.32%, based on the weight of the solid product, of sulfur dioxide.

The entire amount of the above reaction mixture was treated with liquid ammonia in a manner similar to that in Comparative Example 2, thereby obtaining 16.47 g of a solid product. This product proved, by analysis, to contain 93.05% of α-aminocyclohexanone oxime hydrochloride. The yield of this compound was 93.08% based on the nitrosyl chloride used.

EXAMPLE 4

Following the procedure set forth in Comparative Example 2, a reaction mixture of cyclohexene and nitrosyl chloride was prepared. Then, 60 g of n-hexane were added thereto, and the sulfur dioxide was removed therefrom in a manner similar to that in Example 1. The light blue reaction so obtained proved, by analysis, to contain 0.27%, based on the weight of the solid product, of sulfur dioxide.

The entire amount of the above reaction mixture was treated with liquid ammonia in a manner similar to that in Comparative Example 2, thereby obtaining 16.53 g of a solid product. This product proved, by analysis, to contain 92.68% of α-aminocyclohexanone oxime hydrochloride. The yield of this compound was 93.05%, based on the nitrosyl chloride used.

What we claim is:

1. An improvement in the process for the amination of bis(2-chloro-1-nitrosocyclohexane) wherein bis(2- chloro-1-nitrosocyclohexane) prepared by reacting cyclohexene with nitrosyl chloride in the presence of liquid sulfur dioxide is treated with ammonia, said improvement comprising evaporating sulfur dioxide to substantially remove it from the reaction mixture in the form of a slurry or solution containing bis(2-chloro-1-nitrosocyclohexane) in the presence of an organic solvent, incorporated into said reaction mixture, which solvent is inert to said reaction mixture, and then, treating the thus prepared slurry or solution of bis(2-chloro-1-nitrosocyclohexane) in the organic solvent with ammonia.

2. A process according to claim 1 wherein said organic solvent is incorporated into the reaction mixture in an amount of 1 to 20 g per g of bis(2-chloro-1-nitrosocyclohexane).

3. A process according to claim 1 wherein said organic solvent has a boiling point lower than 120° C at atmospheric pressure, and is at least one member selected from the group consisting of hydrocarbons, halogenated hydrocarbons and alcohols having 1 to 4 carbon atoms.

4. A process according to claim 3 wherein said organic solvent is cyclohexene.

5. A process according to claim 1 wherein said evaporation of sulfur dioxide is carried out at a temperature not exceeding 50° C.

6. A process according to claim 1 wherein said evaporation of sulfur dioxide is carried out to an extent such that the content of sulfur dioxide in the reaction mixture becomes less then approximately 0.5% by weight based on the weight of bis(2-chloro-1-nitrosocyclohexane).

7. A process according to claim 1 wherein the slurry or solution of bis(2-chloro-1-nitrosocyclohexane) in the organic solvent is treated with more than 20 moles, per mole of bis(2-chloro-1-nitrosocyclohexane), of ammonia at a temperature of 50° to 90° C and at a high pressure, for a period of 15 minutes to 2 hours.

* * * * *